(12) United States Patent
Law et al.

(10) Patent No.: US 9,016,967 B2
(45) Date of Patent: Apr. 28, 2015

(54) APPLICATORS (75) Inventors: Brian Robert Law, Leicester (GB); David John Pritchett, Ashby de la Zouch (GB)

(73) Assignee: Rieke Corporation, Auburn, IN (US)

( * ) Notice: Subject to any disclaimer, the term of this patent is extended or adjusted under 35 U.S.C. 154(b) by 0 days.

(21) Appl. No.: 13/369,870

(22) Filed: Feb. 9, 2012

(65) Prior Publication Data
US 2012/0219347 A1    Aug. 30, 2012

Related U.S. Application Data (63) Continuation of application No. PCT/GB2010/001522, filed on Aug. 10, 2010.

(30) Foreign Application Priority Data

Aug. 10, 2009 (GB) .................................. 0913973.4

(51) Int. Cl.
B43K 5/14 (2006.01)
A61F 13/40 (2006.01)

(52) U.S. Cl.
CPC .................................. A61M 35/006 (2013.01)

(58) Field of Classification Search
USPC ......... 401/134, 205, 207, 284, 135, 206, 263, 401/264, 203, 204; 604/2, 3
See application file for complete search history.

(56) References Cited

U.S. PATENT DOCUMENTS

| 2,976,560 | A | 3/1961 | Turner |
| 2,998,822 | A | 9/1961 | Birch et al. |
| 3,324,855 | A | 6/1967 | Heimlich et al. |
| 3,349,966 | A | 10/1967 | Schartzman |
| 3,399,020 | A | 8/1968 | Margolis et al. |
| 3,519,364 | A | 7/1970 | Truhan |
| 3,601,287 | A | 8/1971 | Schwartzman |

(Continued)

FOREIGN PATENT DOCUMENTS

| DE | 20 2005 012686 U1 | 10/2005 |
| WO | WO 84/04794 | 11/1985 |

(Continued)

OTHER PUBLICATIONS

Intnernational Search Report and Written Opinion for WO 2011/018622 dated Jan. 27, 2011.

(Continued)

*Primary Examiner* — David Walczak
*Assistant Examiner* — Bradley Oliver
(74) *Attorney, Agent, or Firm* — Woodard Emhardt Moriarty McNett & Henry LLP (57) ABSTRACT

Applicators are described suitable for the application of liquid to patient's skin. An applicator pad (3) is supported on a support flange (23) of an applicator housing (2), which receives a liquid cartridge (5). To moderate the rush of liquid on to the back of the applicator pad a flow distributor plate (6) is positioned on the rear position of the pad (3), restricting flow onto the pad to an annular slit opening around the plate (6). The front surface of the plate (6), opposing the pad (3), may have one or more grooves so that liquid can flow from the edge towards the center. Also disclosed, as an alternative, is the use of a projecting cantilevered tongue structure to distribute liquid across the rear surface of the sponge pad. The pad may have a hooked lobe shape for a front end of the applicator pad.

36 Claims, 12 Drawing Sheets

(56) References Cited

U.S. PATENT DOCUMENTS

| | | |
|---|---|---|
| 3,636,922 A | 1/1972 | Ketner |
| 3,891,331 A | 6/1975 | Avery |
| 4,084,910 A | 4/1978 | LaRosa |
| 4,140,409 A | 2/1979 | DeVries |
| 4,148,318 A | 4/1979 | Meyer |
| 4,173,978 A | 11/1979 | Brown |
| 4,183,684 A | 1/1980 | Avery, Jr. |
| 4,201,491 A | 5/1980 | Kohler |
| 4,225,254 A | 9/1980 | Holberg et al. |
| 4,415,288 A | 11/1983 | Gordon et al. |
| 4,498,796 A | 2/1985 | Gordon et al. |
| 4,507,111 A | 3/1985 | Gordon et al. |
| 4,578,055 A | 3/1986 | Fischer |
| 4,863,422 A | 9/1989 | Stanley |
| 4,925,327 A | 5/1990 | Wirt |
| 5,006,004 A | 4/1991 | Dirksing et al. |
| 5,015,228 A | 5/1991 | Columbus et al. |
| 5,019,033 A | 5/1991 | Geria |
| 5,088,849 A | 2/1992 | Johnson et al. |
| 5,147,337 A | 9/1992 | Plone |
| 5,288,159 A | 2/1994 | Wirt |
| 5,308,180 A | 5/1994 | Pournoor et al. |
| 5,435,660 A | 7/1995 | Wirt |
| 5,445,462 A | 8/1995 | Johnson et al. |
| 5,489,280 A | 2/1996 | Russell |
| 5,509,744 A | 4/1996 | Frazier |
| 5,568,988 A | 10/1996 | Knox et al. |
| 5,658,084 A | 8/1997 | Wirt |
| 5,713,843 A | 2/1998 | Vangsness |
| 5,769,552 A | 6/1998 | Kelley et al. |
| 5,775,826 A | 7/1998 | Miller |
| 5,791,801 A | 8/1998 | Miller |
| 5,871,297 A | 2/1999 | Rogers et al. |
| 5,908,256 A | 6/1999 | Bernstein |
| 5,934,296 A | 8/1999 | Clay |
| 6,190,367 B1 | 2/2001 | Hall |
| 6,238,117 B1 | 5/2001 | Griebel et al. |
| 6,371,675 B1 | 4/2002 | Hoang et al. |
| 6,422,778 B2 * | 7/2002 | Baumann et al. ............ 401/134 |
| 6,471,095 B1 | 10/2002 | Cann |
| 6,475,701 B2 | 11/2002 | Ohno et al. |
| 6,488,665 B1 | 12/2002 | Severin et al. |
| 6,505,985 B1 | 1/2003 | Hidle et al. |
| 6,533,484 B1 | 3/2003 | Osei et al. |
| 6,536,975 B1 | 3/2003 | Tufts |
| 6,595,696 B1 | 7/2003 | Zellak |
| 6,616,363 B1 | 9/2003 | Guillaume et al. |
| 6,672,784 B2 | 1/2004 | Baumann et al. |
| 6,689,103 B1 | 2/2004 | Palasis |
| 6,729,786 B1 | 5/2004 | Tufts et al. |
| 6,743,211 B1 | 6/2004 | Prausnitz et al. |
| 6,755,586 B1 | 6/2004 | Frazier |
| 6,773,193 B2 * | 8/2004 | Delage .......................... 401/205 |
| 6,805,682 B1 | 10/2004 | Campbell |
| 6,811,341 B2 | 11/2004 | Crane |
| 6,869,242 B2 | 3/2005 | May |
| 6,909,339 B2 | 6/2005 | Yonekura et al. |
| 6,910,822 B2 | 6/2005 | Hidle et al. |
| 6,916,133 B2 | 7/2005 | Hoang et al. |
| 6,916,137 B2 | 7/2005 | Shiraiwa |
| 6,991,394 B2 | 1/2006 | Tufts et al. |
| 7,090,422 B2 | 8/2006 | Baumann et al. |
| 7,201,525 B2 | 4/2007 | Mohiuddin |
| 7,261,701 B2 | 8/2007 | Davis et al. |
| 7,866,907 B2 | 1/2011 | Cable, Jr. et al. |
| 8,002,486 B1 * | 8/2011 | Tran ............................ 401/206 |
| 8,113,731 B2 | 2/2012 | Cable, Jr. et al. |
| 8,348,537 B2 | 1/2013 | Cable, Jr. et al. |
| 2001/0055511 A1 | 12/2001 | Baumann et al. |
| 2002/0076255 A1 | 6/2002 | Hoang et al. |
| 2002/0076258 A1 | 6/2002 | Crosby et al. |
| 2003/0049069 A1 | 3/2003 | Osei et al. |
| 2003/0060746 A1 | 3/2003 | Mark |
| 2003/0068190 A1 | 4/2003 | Hidle et al. |
| 2003/0118629 A1 | 6/2003 | Scholz et al. |
| 2003/0149106 A1 | 8/2003 | Mosbey et al. |
| 2003/0194447 A1 | 10/2003 | Scholz et al. |
| 2004/0068218 A1 | 4/2004 | Davis et al. |
| 2004/0114988 A1 | 6/2004 | Baumann |
| 2004/0162533 A1 | 8/2004 | Alley |
| 2004/0179888 A1 | 9/2004 | Tufts et al. |
| 2004/0240927 A1 | 12/2004 | Hoang et al. |
| 2004/0267182 A1 | 12/2004 | Davis et al. |
| 2006/0039742 A1 * | 2/2006 | Cable et al. .................. 401/207 |
| 2006/0072962 A1 * | 4/2006 | Cybulski et al. ............. 401/205 |
| 2007/0147947 A1 | 6/2007 | Stenton |
| 2007/0292193 A1 * | 12/2007 | Lee et al. ...................... 401/205 |
| 2009/0320856 A1 | 12/2009 | Brewer et al. |
| 2011/0284583 A1 | 11/2011 | Fazzolari |

FOREIGN PATENT DOCUMENTS

| | | |
|---|---|---|
| WO | WO 85/04794 A1 | 11/1985 |
| WO | WO 94/13352 A1 | 6/1994 |
| WO | WO 95/03734 | 2/1995 |
| WO | WO 99/51184 A1 | 10/1999 |
| WO | WO 00/10889 | 3/2000 |
| WO | WO 02/49708 A2 | 6/2002 |
| WO | WO 2004/062709 | 7/2004 |
| WO | WO 2006/131747 | 12/2006 |

OTHER PUBLICATIONS

International Search Report and Written Opinion for WO 2011/018621 dated Mar. 29, 2011.

* cited by examiner

APPLICATORS

CROSS REFERENCE TO RELATED APPLICATIONS

This application is a continuation of International Application No. PCT/GB2010/001522 filed Aug. 10, 2010, which claims the benefit of GB 0913973.4 filed Aug. 10, 2009, both of which are hereby incorporated by reference.

BACKGROUND

This invention has to do with applicators useful for applying surgical prep liquids to the skin.

The conventional preparation of a patient's skin for surgery includes an extended period of cleaning using soap or the like, followed by the application of an antiseptic or disinfectant. The nature, duration and difficulty of this task depend heavily on the kind of surgical procedure to be followed, and on the size, shape and orientation of the body parts involved.

The oldest—and still widespread—method of applying the disinfectant is by dipping a swab, sponge or pad, held in forceps, into a dish of liquid and wiping it over the skin. Spent swabs/pads are continually discarded and fresh ones taken. The disinfectant is usually alcohol-based and may contain ingredients (such as iodine) that can irritate or burn the skin. It is important that the rate of application of solution be controlled, so that excess does not flow away to unintended areas, or form pools underneath the body or in hollows of the body where it may burn or irritate the patient, or indeed be a fire hazard if a cauterisation procedure is used. It is generally desirable to avoid mess or spillage whether on the patient's body or elsewhere. Another reason for keeping the applied liquid under control is to avoid liquid which has contacted one region of the patient's skin flowing away (or being carried on the applicator) so that it then contacts another region.

Conversely, and despite all the above factors indicating careful application, surgical prep is often done under severe time pressure and subject to safety and effectiveness there is every interest in doing it as quickly as possible.

Over the years many proposals have been made for handheld applicator devices for applying surgical prep solution, incorporating an applicator head with a pad, sponge or other soft or deformable permeable element to be wiped across the skin, and a reservoir of the surgical prep solution—often contained in a handle of the device—communicating with the applicator pad to feed solution. This can make the application more efficient by obviating the repeated dipping of swabs and the discarding and replacement of spent swabs. By providing the solution in a sealed sterile reservoir or cartridge, which can be opened by engaging it appropriately with an applicator head (e.g. by a spike built into the applicator head rupturing a membrane or film closure on the front of the cartridge) operation of these devices is made easy. Nevertheless these are devices which, although used under time pressure and needing to be reliable, must be of simple and economical construction since they may be used only once. With these constraints, it has been quite difficult to produce a cost-effective device with which the application of prep solution to the skin is really controllable and convenient while being adaptable to different preferences of surgeons and their assistants. There is much room for improvements to be made.

In the present disclosure, we address issues of distributing liquid flow to a permeable, deformable applicator member such as a sponge element, and of controlling the flow between a liquid supply reservoir and the permeable applicator element.

As regards distribution of flow, WO2006/041801 describes an applicator having a flat permeable applicator pad on the front face of a distributor element which provides sub-divided chambers behind the pad, each chamber receiving prep solution from the reservoir.

U.S. Pat. No. 4,415,288 has an applicator sponge block exposed on both oppositely-directed major faces, receiving liquid from the handle reservoir along a conduit with an enlarged perforated end chamber embedded in the centre of the sponge block. An alternative has a flat paddle-shaped projection into the sponge interior, with a liquid feed to each face of the paddle from a hole adjacent its root.

WO01/74436 discloses a flat rectangular sponge pad with a back face fixed to a flat rectangular spreader plate the same size as the pad. Solution enters through a central hole of the spreader plate, which has a pattern of radiating channels on its front face to assist flow towards the edges of the back of the foam pad. A small film pad may be positioned in front of the central opening, to encourage outward flow along the channels.

U.S. Pat. No. 4,925,327 suggests inserting a porous layer over the rear surface of the applicator pad.

SUMMARY

One object of the present disclosure is to provide new and useful applicator constructions with means for controlling or regulating liquid flow immediately upstream of the applicator pad.

Generally the proposals, as represented by the content of the present disclosure, are implemented in an applicator having a deformable, liquid permeable applicator pad, preferably of resilient sponge material. The applicator pad has a front surface intended for contact with the skin, and a back surface connected to a pad support portion of the applicator. Preferably the applicator pad is in layer form. It may be substantially flat. Preferably its layer thickness is less than the smallest linear dimension (e.g. length, width) of its front application surface.

According to a first proposal, or embodiment, flow access to the rear of the pad is through a generally annular slit opening. This opening is preferably defined between the outer periphery of a flow distributor element, e.g. in the form of a plate, covering a central region of the pad rear surface, and a pad support component engaging around the pad rear surface at a slit spacing from the edge of the distributor element.

The annular slit is not necessarily a true or complete circle; it may have any outline consistent with distributing the fluid over the back surface of the pad. Additionally, there may be provided one or more recessed spur channels defined by the face of the pad support component adjacent the pad which intersect and extend from the annular slit to further distribute the fluid over the back surface of the pad.

A second proposal, or embodiment, combinable with the first, is that the flow distribution arrangement includes a flow distributor element, e.g. plate, covering a region (such as a central region) of the back of the applicator pad. The front surface of the distributor element (directed forwards against the pad) preferably defines one or more recessed flow channels for supplied liquid to flow in a direction towards the centre of the distributor element.

According to this proposal, the distributor element covers a region of the applicator pad rear surface against direct liquid access from the rear but enables a controlled flow of liquid to this region from the edge of the distribution element along one or more of the flow channels at the front of the distributor element.

Preferably plural flow channels extend from the edge towards the centre of the distributor element. One flow channel may be intersected by one or more others. For example, one or more generally radial channels may be intersected by one or more generally circumferential channels (using these terms in a general sense in relation to a centre of the fluid access region, not necessarily implying a strictly circular geometry). Or, there may be a larger recessed (liquid-holding) zone on the front of the distribution element, to which one or more channels lead.

Preferably the distributor element is closed (impermeable) over its entire area except around the edges.

In the above aspects, the distributor element is desirably a generally flat plate, e.g. disc. In one preferred construction, this plate—preferably over most of its area—forms a floor of an antechamber or release reservoir, typically formed in a neck of the applicator immediately above (behind) the pad support portion. Upstream of this antechamber is a flow entry construction which may have a narrower flow cross-section than the antechamber.

This flow entry construction typically comprises an entry structure or entry mechanism by means of which liquid enters the antechamber from a discrete container of liquid, such as a cartridge or vial having a rupturable or otherwise openable front end wall. Containers of this general kind are known for use in applicators of the present kind, as mentioned above. The applicator includes an interior structure or mechanism for opening the container when it is advanced into engagement with the structure. There may be e.g. a cutter or spike which ruptures a wall or film of the container, or an abutment which breaks off a frangible nose portion thereof or opens a displaceable wall portion thereof. In any event, there may be some relative restriction of flow at this region after opening. By providing an antechamber of substantial volume downstream of it, it can be arranged that from the time of opening of the container—when the pressure head is maximum—a body of liquid is promptly formed in the antechamber to feed the applicator pad directly but not excessively quickly via the flow distributor path discussed above.

In a preferred embodiment, an outer wall of the applicator flow conduit (preferably the wall of an antechamber as mentioned above) at the front end thereof expands outwardly (e.g. integrally) into a flange formation constituting a support for the rear of the pad, and desirably having substantially the same outline shape as the rear of the pad, or a congruent shape.

A peripheral part of this flange formation can be bonded to the rear of the pad to hold the pad in place. Inside the bonded peripheral part the front surface of the support flange can retain the flow distributor plate in a recessed zone corresponding substantially in size and shape to the distribution plate, but with a flow clearance around its periphery, e.g. a slit clearance.

The clearance may be defined by rearward spacing between the flow distributor plate periphery and a forwardly-directed shoulder of the applicator housing flange behind it, and/or by radial clearance between the periphery of the distributor plate and an inwardly-directed border of a flange opening in which it sits. The front surface of the distributor plate desirably lies directly against the back surface of the applicator pad. The back surface of the distributor plate is exposed to a liquid in the fluid supply conduit, and preferably in an antechamber as mentioned above.

The distributor plate may be fixed in place relative to the applicator housing, e.g. by being bonded or welded thereto, or trapped by fitting closely in the recess between the components. Alternatively the distributor plate may be movable in its recess relative to the applicator housing, and function as a valve. For this, the periphery of the flow conduit may present an annular sealing surface region, desirably forwardly-directed, and the distributor plate or distributor element presents a corresponding annular counter-surface. In a forward position of the distributor plate/element the sealing surface and counter-surface are spaced to allow flow around the plate/element, while in a rearward position of the plate/element, those surfaces contact to block flow. For example, a forwardly-directed annular shoulder of the applicator housing flange and a rearwardly-directed edge portion around the distributor plate may contact to provide this valve function. Contact is driven by pressing harder on the pad, either deliberately to stop the flow or inadvertently, in which case the stopping of flow may be advantageous in preventing liquid from being squeezed out of the pad and back into the flow conduit.

In a third proposal or embodiment as disclosed herein, optionally combinable with the first or second, the flow distribution arrangement includes one or more flow distributor limbs or tongues, projecting forwardly from a flow entry construction (such as described above in relation to the second proposal) and extending out into a flow conduit space or antechamber to a position above the back of the applicator pad. The or each distributor limb or tongue is desirably cantilevered out into this space or antechamber. When liquid enters the applicator from the flow entry structure (typically from the newly-opened front end of a cartridge), it has a tendency to flow preferentially down the wall of the flow conduit especially if this is inclined. By providing one or more elements projecting out into the space, surface tension causes liquid to flow out into the middle of the space along the element and fall or flow from its end or periphery (according to its shape) and thereby be distributed more evenly in relation to the pad. It may fall directly onto the pad, or there may be an intervening flow distributor element or plate e.g. as described above. Desirably the distributor tongue or limb is shaped to have one and preferably plural downward edges distributed across the antechamber or conduit space, to encourage liquid to fall off in a distributed pattern. Subdivision of the tongue or limb by way of branching or apertures is a means of achieving this.

A further proposal or embodiment, again combinable with any one or any combination of the above proposals, relates to the shape of the applicator pad. Preferably the pad is in layer form with a front contact surface for contact with the skin, the opposed back surface being mounted against the applicator body or housing, and with a narrow side edge face usually exposed. The plan outline of the pad may take any of various shapes, for example generally rectangular, circular or trapezoidal as in prior art proposals. However we particularly prefer that the outline has at least one corner or angle subtending less than 90 degrees, such as the point of a triangular outline or of an oval, heart- or teardrop-shaped outline. In particular we propose that the pad outline may include a relatively narrow lobe portion adjacent which the outline has a concave part, so that the lateral dimension at the lobe portion decreases sharply relative to a main region of the pad. Such a lobe portion, particularly with exposed side edge faces as mentioned, is very useful for applying surgical prep liquid into narrow spaces such as between fingers and toes. A particularly preferred embodiment the lobe has a hooked formation, with a concave approach outline on only one side and the other side being straight or convex. Typically such an applicator has a handle portion inclined obliquely to the pad. Preferably the handle inclines away from such a lobe portion.

Especially with a hooked lobe, a natural hand action enables application of solution into crevices of a patient's body.

BRIEF DESCRIPTION OF THE DRAWINGS

Embodiments of our proposals are now described by way of example, with reference to the accompanying drawings in which.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 1:
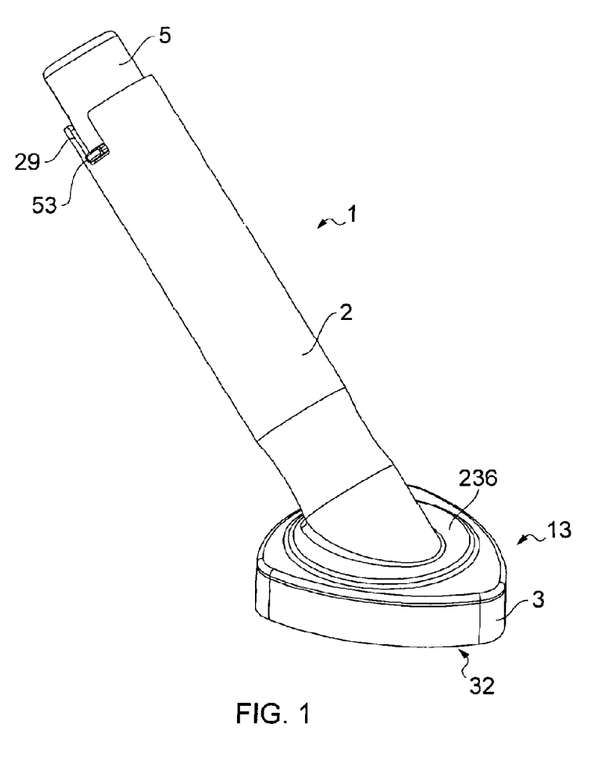
FIG. 1 is a perspective view of a first embodiment of surgical prep dispenser.
Figure 2:
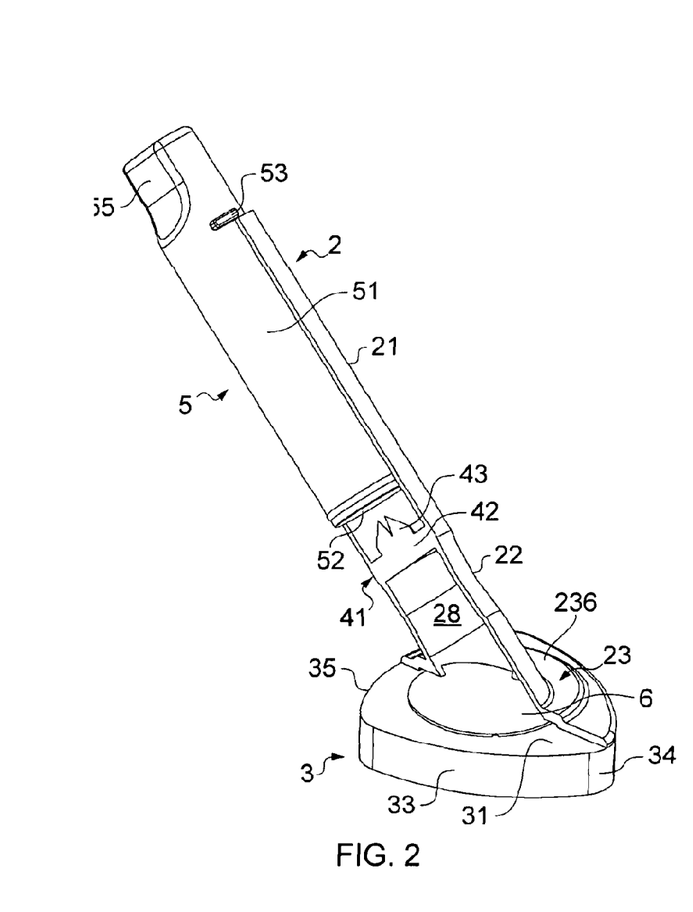
FIG. 2 is a partial axial section of the FIG. 1 dispenser, showing a distributor plate.

With reference to FIGS. 1 and 2, a surgical prep dispenser or applicator includes a pad portion 13 and a handle portion 1. The handle 1 is inclined e.g. at about 45 degrees to the plane of the pad portion 13, so that the flat front face 32 of a sponge pad 3 of the pad portion 13 is easily applied to body surfaces by a person holding the handle 1 in one hand.

Referring also to FIG. 2, the handle structure consists of a tubular applicator casing 2 with an open top end receiving a cylindrical cartridge 5 containing disinfectant liquid of any suitable kind (as well known to a skilled person). The main cartridge casing 51 is a close fit in the applicator casing 2. Its front end is closed off by a foil or film seal layer 52. Its top end has a finger-grip portion 55 and a projecting lug 53.

The applicator casing or housing 2 is a generally tubular single piece of moulded plastics. Part-way along its length it has an internal structure 41 which serves as an opener for the cartridge 5 and as a flow entry to the head portion of the applicator or dispenser. In the present embodiment, in a generally conventional fashion, it consists of an open cruciform support with sharp cutter projections 43 projecting rearwardly towards the front of the cartridge. Forwardly of this flow entry/cutter structure 41, the applicator casing 2 has a tubular wall portion 22 enclosing an antechamber 28 leading to an opening where the tube wall diverges as a flange 23 to whose front surface the sponge pad 3 is bonded. The support flange 23 assists application of liquid by the entire area of the pad 3 with even pressure.

Figure 3:
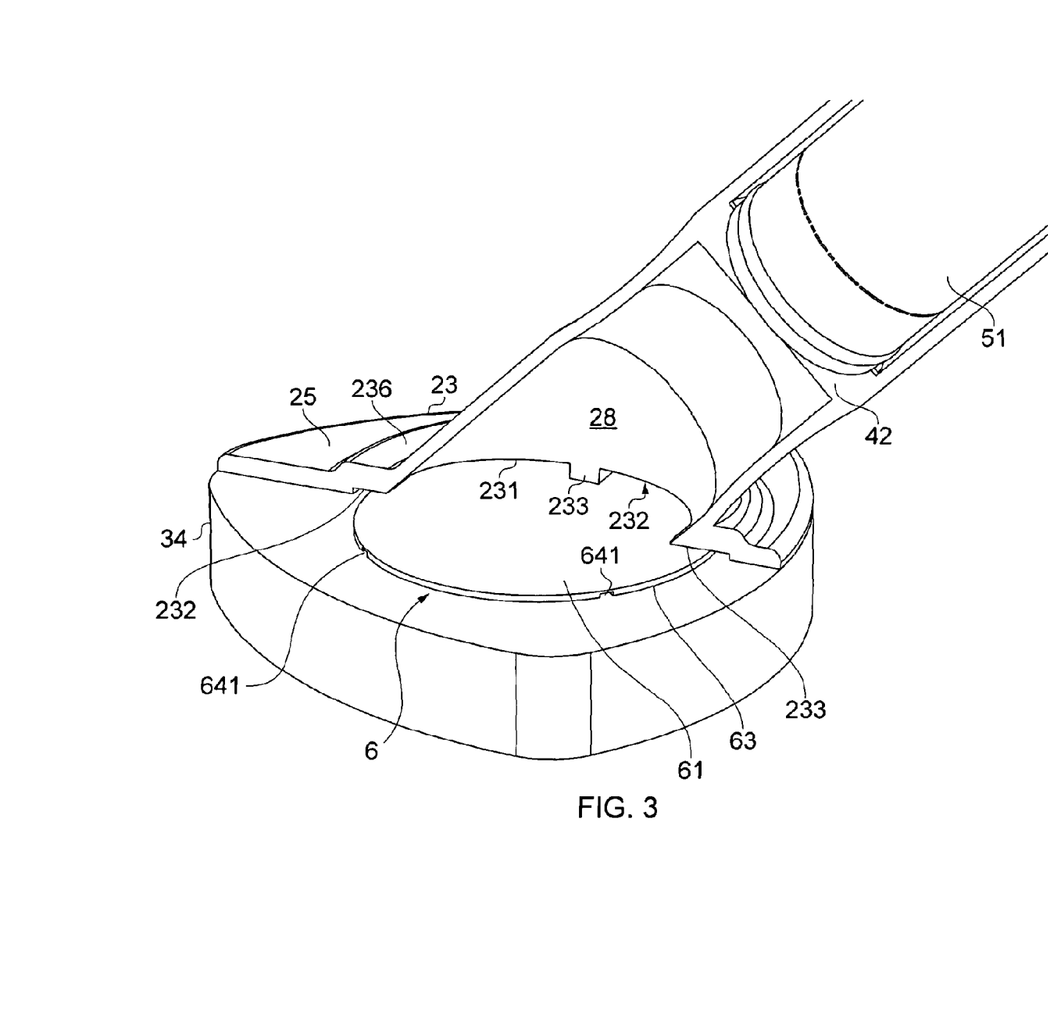
FIG. 3 shows the FIG. 2 distributor plate construction enlarged, in one version.

Referring additionally to FIG. 3, the sponge pad 3 has exposed side edges 33 and its shape—like that of the support flange 23—is a somewhat rounded triangle with a smallest angle or point 34 at the front end (directed away from the handle) and broader angles at its rear edge 35. The material of the sponge pad 3 is not critical and can be chosen from known options. The front point 34 is useful for applying surgical prep solution to more intricate parts of the body surface.

Figure 4:
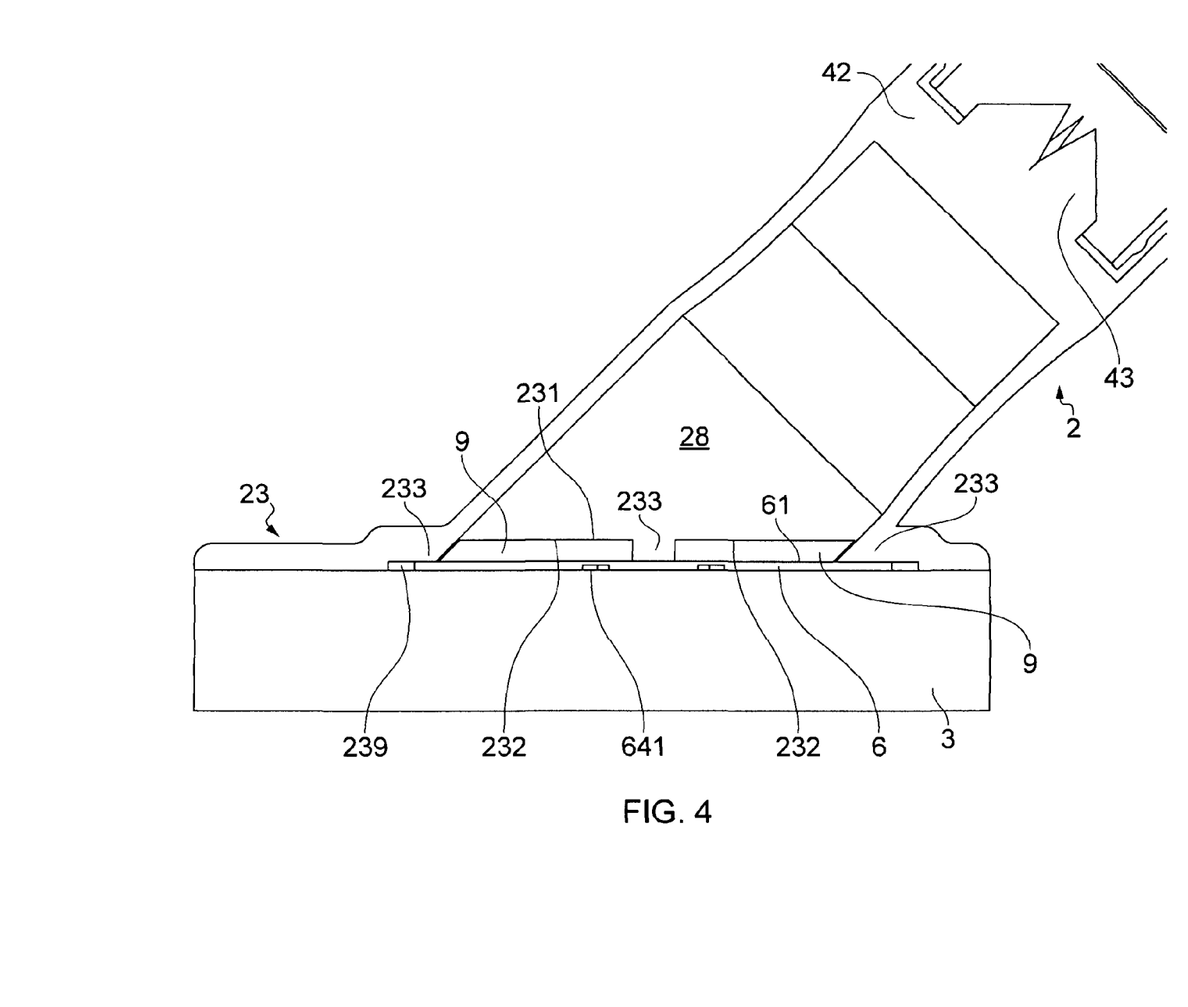
FIG. 4 is a full section through the distributor plate and pad construction of FIG. 3.

Referring to FIGS. 2 and 3, a flow distributor disc 6, essentially in the form of a thin flat plastics plate, is trapped between the front of the applicator casing 2 and its flange 23 above and the sponge pad 3 below. The distributor disc 6 is circular (in this embodiment) and larger in area than the (elliptical) opening of the casing tube whose edge 231 is indicated in FIG. 3. Around this oval opening the flange 23 has a circular raised portion 236, slightly larger than the distributor disc 6, defining on its underside a downwardly-directed annular recess or shoulder 232 (FIGS. 3, 4) facing down with a slight overlap all around (more at the sides because of the shape difference) onto the edge 63 of the disc 6. The shoulder is interrupted by four integral downward locating lugs 233 which contact directly the top surface 61 of the distributor plate 6 and trap it against the top surface of the pad 3 as seen in FIG. 4. The radially-inwardly directed surround surface 239 (FIG. 4) of the recess or shoulder 232 is circular, and has a slight radial spacing from the edge 63 of the disc 6. Moreover, in the long arcuate intervals between the lugs 233, the edge 231 of the casing opening stands clear above the top of the distribution disc by an annular slit spacing 9 (FIG. 4) through which fluid from the antechamber 28 can pass freely to the edge of the disc 6 and down around that edge onto the sponge pad 3.

Figure 7:
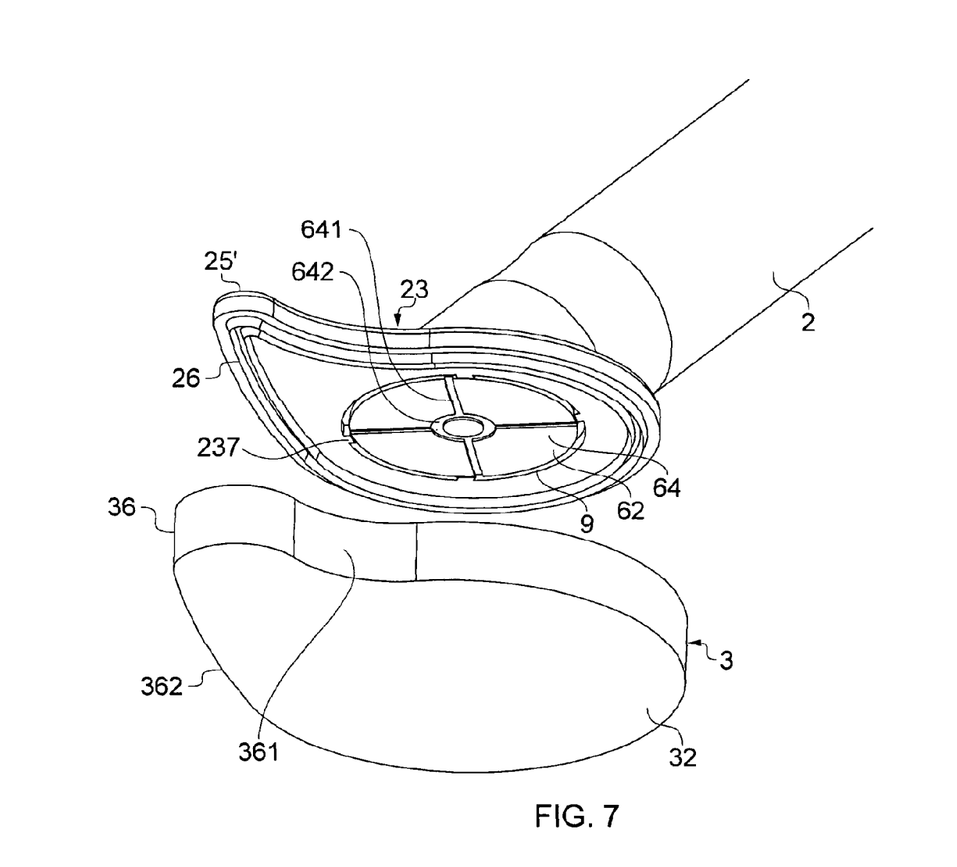
FIG. 7 shows a second embodiment with a hooked pad, the pad being detached to show the underside of a securing flange and distributor plate.

The front face 62 of the distributor disc 6 is shown in FIG. 7, which relates to a different applicator embodiment but the disc is the same. A pattern of recessed channels 64—in this case four radial channels 641 and a central annulus or recessed zone 642—are provided on the front surface. These open at the edge of the disc at openings 641 indicated in FIGS. 3 and 4. FIG. 7 also shows a centring structure for the disc, namely lugs 237 which keep the disc 6 central in relation to the flange 23 and keep the area of the annular slit opening 9 generally uniform around the disc.

Use is initiated in a generally known manner. The cartridge 5 of disinfectant liquid is in a retracted position, maintained by the lug 53 resting against the top edge of the guide casing 21 (FIG. 2). This keeps its front foil or film 52 clear of the cutter 43. The top grip 55 is used to turn the cartridge 5 and bring the lug 53 into register with a notch 29 in the guide casing and it is pushed in (FIGS. 1, 3), the cutter 43 then rupturing the foil or film 52 and the liquid immediately flowing out of the cartridge, past the open cross-form support 42 and into the antechamber 28 at the front of the device.

Were the liquid to flow directly onto the back surface of the sponge pad 3 at this juncture, results would be poor. Much of the liquid would enter the sponge via the shortest and lowest route, towards the right of FIG. 3, so that not all of the sponge and in particular not the useful forward parts would be properly wetted and replenished. Moreover the overall flow rate of liquid would tend to be too high and uncontrollable. The distributor disc 6 with its predetermined annular slit cap 9 avoids these difficulties by forcing the liquid to pass out to the periphery of the disc before it can reach the sponge at all. It contacts the sponge initially in a distributed annular region. Moreover it can flow inwardly back towards the centre via the channels 64 on the front of the disc. The middle of the sponge therefore gets a moderate supply instead of an excessive supply. The outer regions of the sponge get an adequate supply instead of an inadequate supply. Also, since the distribution of the liquid around the sponge is determined primarily by the relative dimensions of disc 6, lugs 233, and channels 64 which are all easily controlled on manufacture of the plastics components concerned, routine trials enable a satisfactory performance to be achieved and then maintained from one device to another. The rate of release of the liquid from the cartridge 51 and the exact effectiveness of the opening of the film 52 by the cutter are not critical, because a body of liquid can lie in the antechamber 28 and gradually reach the pad 3 through the annular slit 9 and this determines the application rate.

Figure 5:
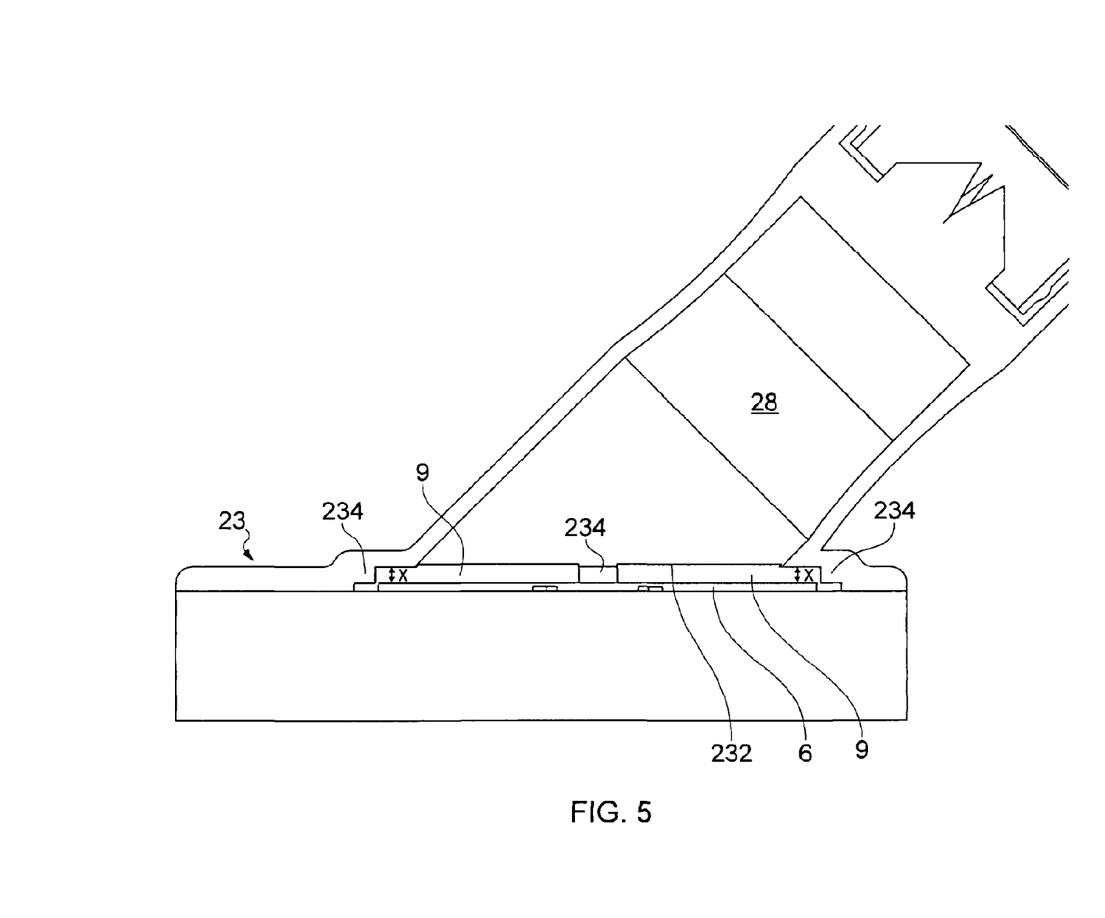
FIG. 5 is a corresponding sectional view of a distributor plate and pad in another version.
Figure 6:
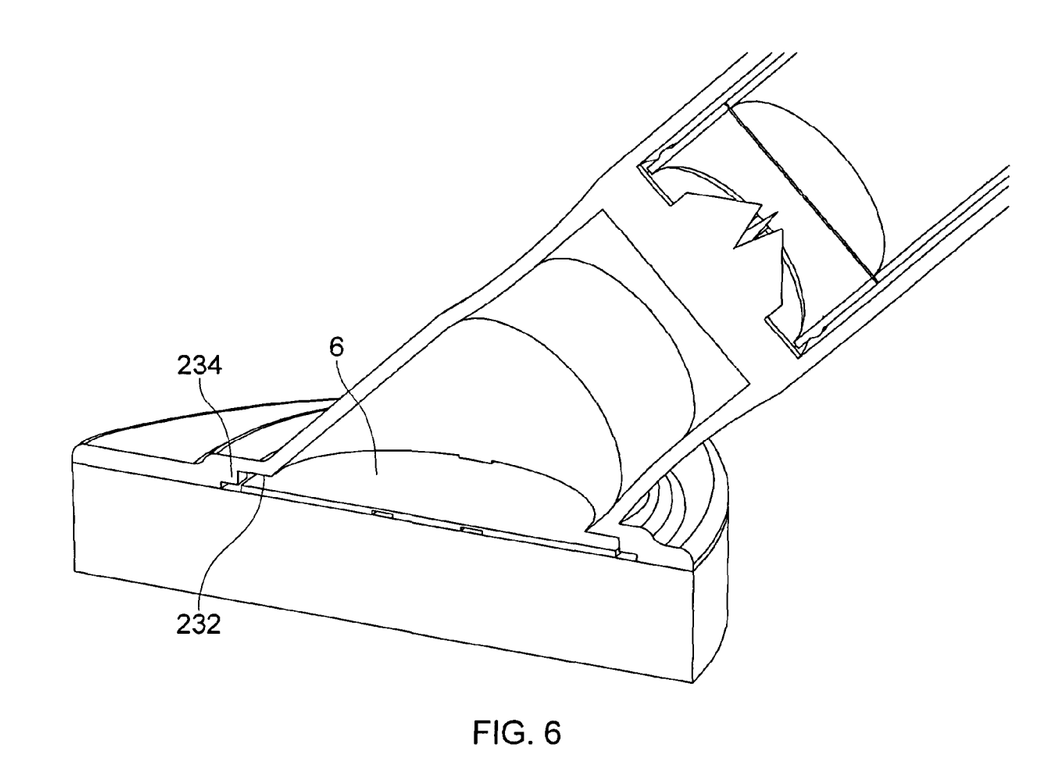
FIG. 6 is a corresponding sectional view of a distributor plate and pad in another version.

FIGS. 5 and 6 show a variant in which the disc 6 is identically constructed but the shoulder formation in the flange 23 is different. Instead of the lugs 233 which positively hold the disc 6 down against the pad, non-overlapping guide lugs 234 are provided which allow the disc 6 to rise up and substantially abut the downward shoulder 232, effectively closing the annular opening 9. Strong pressure on the pad 3 will cause this. It closes the fluid flow path between the antechamber 28 and the pad 3. This avoids the possibility that liquid already in the sponge, which may already have been exposed to contamination, passes back into the antechamber 28 and is transferred to another location. Additionally or alternatively, it provides the means for the user to stop the flow deliberately.

The skilled person will appreciate that the distributor disc can still have a useful effect without the recesses or channels on its front surface. Also, different patterns of channels could be used. The present embodiments show a flat circular disc. This gives manufacturing and assembly convenience but the distribution function does not necessarily require these shapes.

FIG. 7 shows a pad 3 and pad support flange 23 of a different shape, having a front point 36 with a sideways hook created by a concave region 361 to one side of the front point and a convex or straight region 362 opposite. The corresponding forward projection 25' of the casing flange 23 is correspondingly hook-shaped to support it. Additionally this figure shows securing ribs or beads 26 projecting down around the underside of the flange 23, to improve bonding or welding strength to the top of the pad 3. This is particularly important when a lobed pad shape is provided, to prevent the front lobe 36 from becoming detached. A skilled person will appreciate that this hooked lobe 36 is easy to insert into small body crevices, e.g. between fingers and toes, at a normal angle of the user's hand.

Figure 7A:
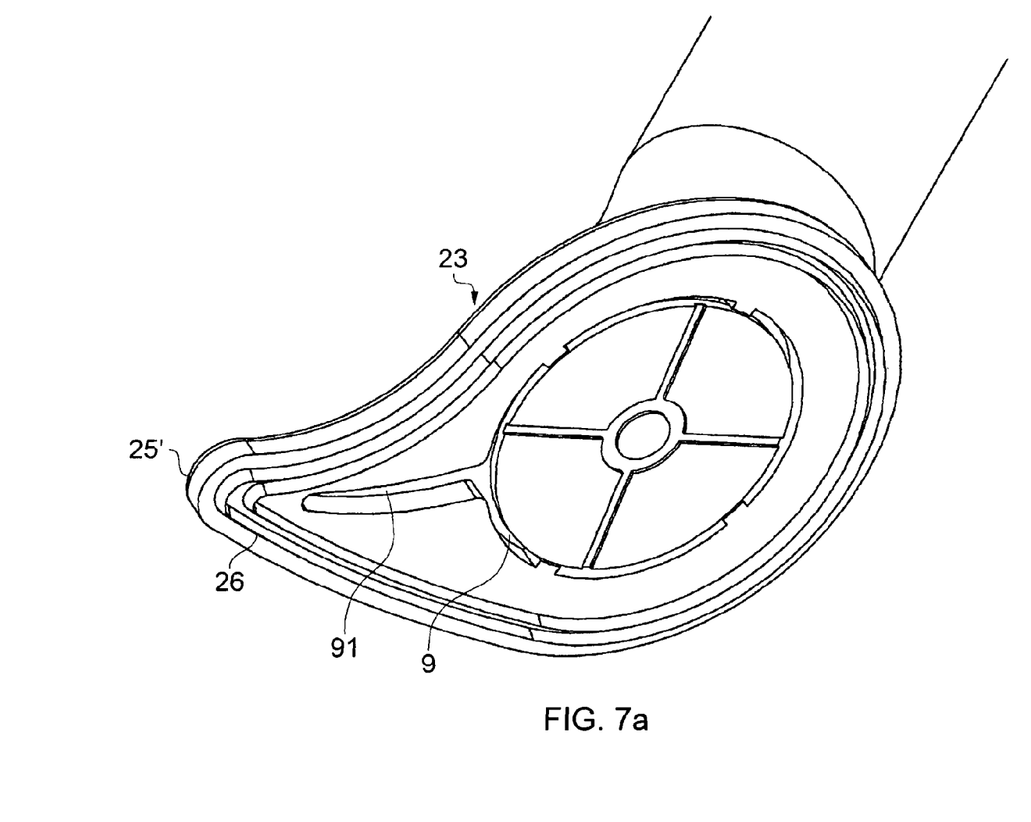
FIG. 7a shows a variant of the underside of the securing flange shown in FIG. 7.

FIG. 7a shows a variant embodiment. Here a spur channel 91 is recessed into the underside of the casing flange 23. The spur channel 91 intersects the annular opening 9 and extends along the underside of the forward projection 25'. When the fluid flows out of the annular opening 9, it can flow along the spur channel to improve fluid supply to the back of the pad in the lobe region.

Figure 8:
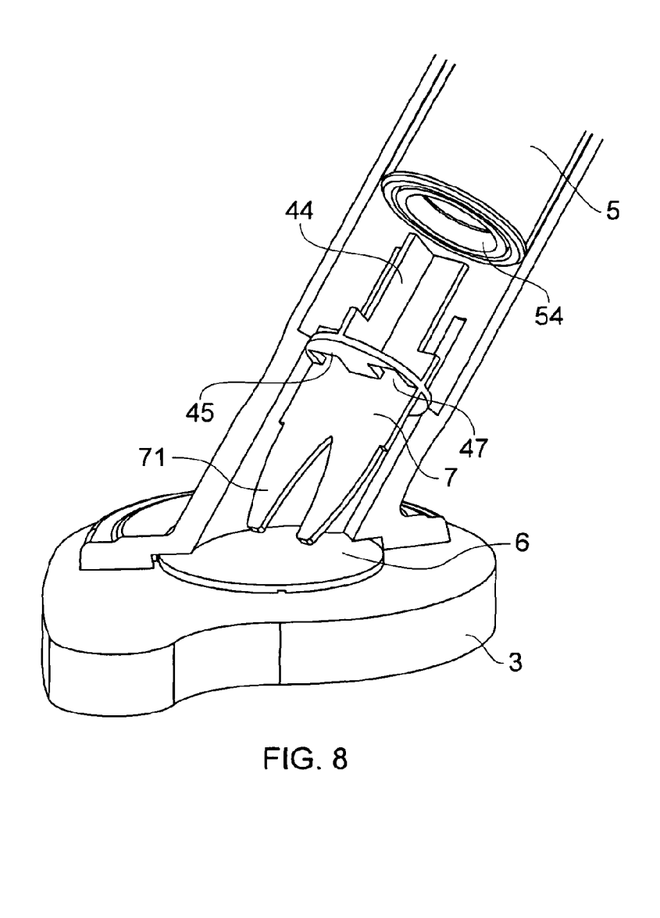
FIG. 8 is a partly-sectioned view of the front end of a third embodiment with a spreader tongue.

FIG. 8 shows a variant embodiment. Here the cartridge 5 is opened by displacing (pushing in) a front wall portion 54 rather than a film, and to this end the cartridge opening structure (flow entry structure) comprises a cruciform-section pusher abutment 44 rather than a cutter. Additionally (and conceptually distinctly) a spreader member or tongue 7 is formed integrally with the partition 45 on which the pusher is mounted, and extends in a cantilevered fashion forwardly and down into the antechamber 28 above the disc 6. The flow entry partition 45 has a substantially closed structure with limited flow openings 47, and these are positioned above the level of the tongue; additionally the pusher blades are formed as closed vanes so that liquid flowing from the cartridge 5 is in large part constrained to flow above them and onto the spreader tongue 7. The tip of the spreader tongue divides into two points 71, aligned above the centre of the distributor disc 6, and it is here that such liquid will pour or drip down. This is in contrast to the previous embodiments, where the liquid would naturally tend to take the shortest and lowest route to one side of the disc, and be fully reliant on the disc for distribution. The present embodiment can achieve a still more even distribution of liquid.

Figure 9:
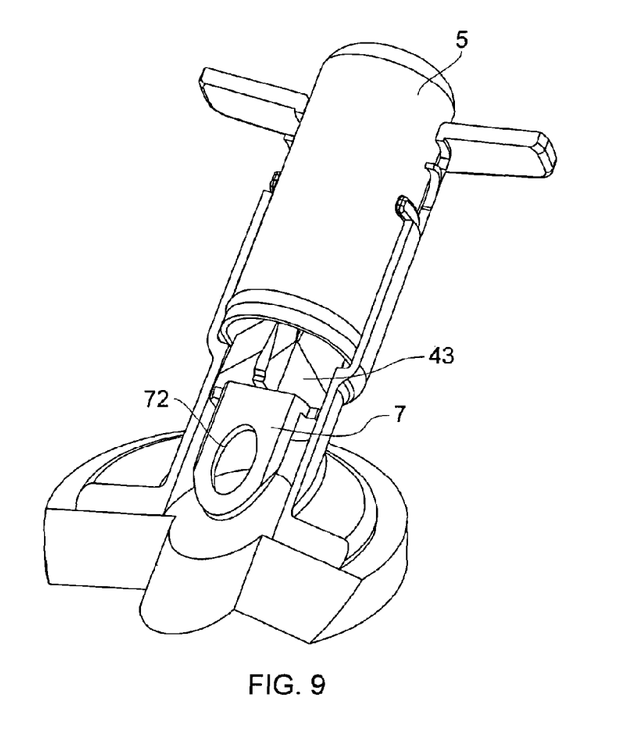
FIG. 9 is a partly-sectioned view of a fourth embodiment with a different spreader tongue.
Figure 10:
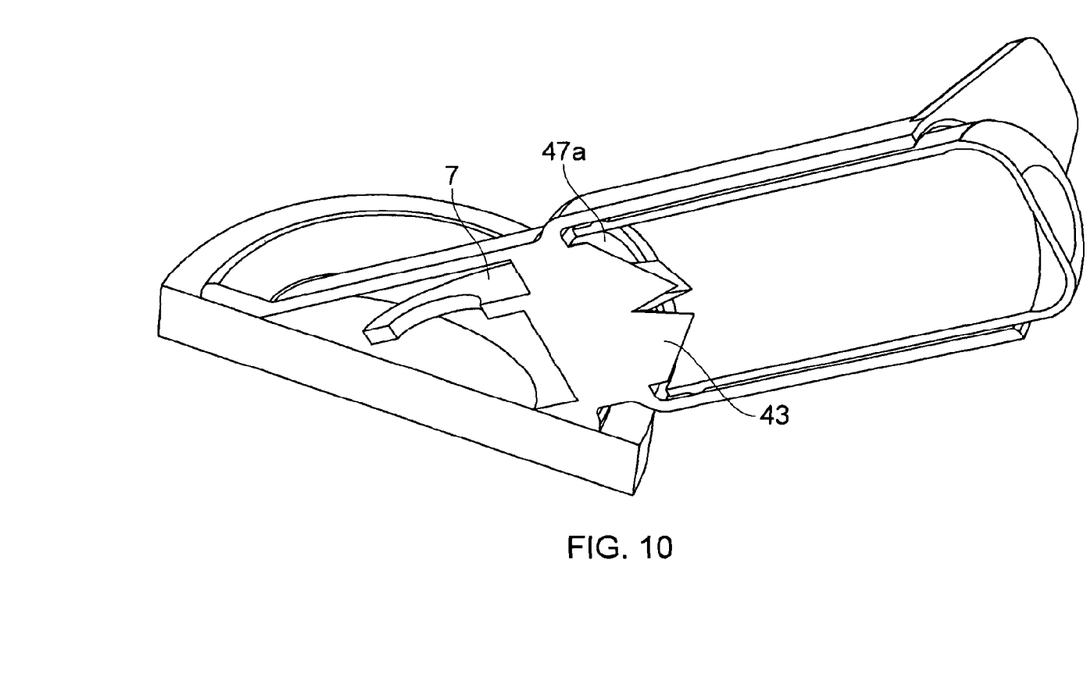
FIG. 10 shows the FIG. 9 dispenser with an orthogonal plane of section to show the position of the spreader tongue.
Figure 11:
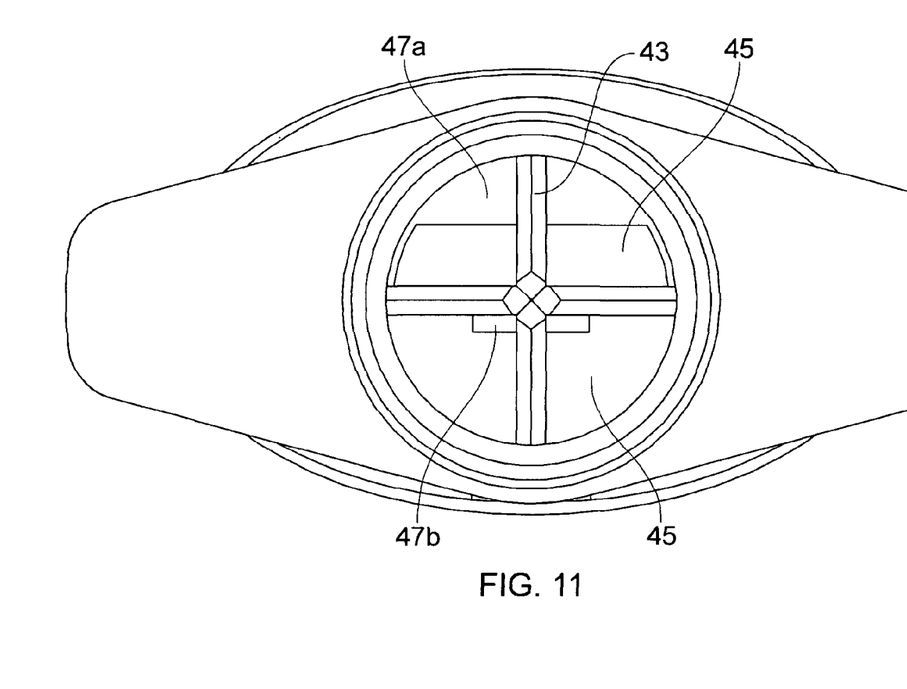
FIG. 11 is an axial view of the fluid entry structure of the fourth embodiment.

FIGS. 9 to 11 show a variant of the spreader tongue idea. This embodiment relies on the spreader tongue 7 for distribution, and does not use a distributor disc 6. The spreader tongue has a central hole 72 to provide a substantial length of downward edge from which liquid can drip. This embodiment uses a cutter 43 as in the first embodiment to open the cartridge 5. However as in the previous embodiment a partition 45 is provided with selective flow holes so that much of the flow goes above the tongue 7 so as to be properly distributed. See FIG. 11, which looks down onto the cutter. The cross-form cutter blades are seen at 43 and as in the previous embodiment they take the form of closed vanes so that liquid does not fall through them. Portions of the partition wall 45 are positioned and dimensioned so that a large flow opening 47a is present at and around the top of the cutter whereas only a small opening 47b exists beneath it. Thus, once the cartridge foil is pierced the main flow passes over the spreader tongue 7, dripping from its peripheral edges and the edges of the hole to distribute the flow over the sponge surface and avoid the problem that most of the liquid would otherwise flow to the nearest part of the sponge.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:
1. A surgical prep applicator comprising:
an applicator housing with a head having a pad support portion;
a deformable, liquid-permeable applicator pad with a rear surface connected to the pad support portion with an outer peripheral edge and a front surface for contact with a patient's skin in use; and
a reservoir of surgical prep liquid being comprised or received in the applicator housing, wherein flow access to the rear surface of the pad is through a generally annular slit which is radially outward of said outer peripheral edge.

2. A surgical prep applicator according to claim 1 in which the applicator pad is substantially flat, and has a layer thickness less than the smallest length or width of its front surface.

3. A surgical prep applicator according to claim 1 in which the plan outline of the applicator pad has at least one angle subtending less than 90°.

4. A surgical prep applicator according to claim 1 in which the applicator housing defines an antechamber immediately above the pad support portion, and a flow entry construction upstream of this antechamber by means of which liquid enters the antechamber from said reservoir which is a discrete container of said surgical prep liquid having an openable front end wall.

5. A surgical prep applicator according to claim 1 in which the applicator housing includes an interior structure for opening a front end wall of a liquid container retaining said surgical prep liquid when the liquid container is advanced into engagement with said interior structure.

6. The surgical prep applicator of claim 1 wherein said applicator pad has an outer edge periphery which includes a narrow lobe portion and a concave portion which is adjacent said narrow lobe portion.

7. A surgical prep applicator comprising:
an applicator housing with a head having a pad support portion;
a deformable, liquid-permeable applicator pad with a rear surface connected to the pad support portion and a front surface for contact with a patient's skin in use; and
a reservoir of surgical prep liquid being comprised or received in the applicator housing, wherein flow access to the rear surface of the pad is through a generally annular slit, wherein said generally annular slit is defined by an outer periphery of a flow distributor element, covering a central region of the pad rear surface, and a pad support component engaging around the pad rear surface at a spacing from the outer periphery of the flow distributor element.

8. A surgical prep applicator according to claim 7 in which the flow distributor element is fluid-impermeable over its area.

9. A surgical prep applicator according to claim 8 in which the front of the distributor element, opposed to the rear surface of the applicator pad, has one or more flow channels whereby liquid may flow from the outer periphery towards the center of the distributor element against the rear surface of the applicator pad.

10. A surgical prep applicator according to claim 9 in which the distributor element is a flat disc.

11. A surgical prep applicator according to claim 10 in which the applicator housing defines an antechamber immediately above the pad support portion, and a flow entry construction upstream of this antechamber by means of which liquid enters the antechamber from said reservoir which is a discrete container of said surgical prep liquid having an openable front end wall.

12. A surgical prep applicator according to claim 11 in which the applicator includes an interior structure or mechanism for opening the front end wall of a liquid container when the container is advanced into engagement.

13. A surgical prep applicator according to claim 7 in which said generally annular slit through which liquid flows to the rear of the pad is defined by rearward spacing between a periphery of a flow distributor element and a forwardly-directed shoulder of an applicator housing flange behind it.

14. A surgical prep applicator according to claim 7 in which the front of the distributor element, opposed to the rear surface of the applicator pad, has one or more flow channels whereby liquid may flow from the outer periphery towards the center of the distributor element against the rear surface of the applicator pad.

15. A surgical prep applicator according to claim 14 in which the distributor element is a flat disc.

16. A surgical prep applicator comprising:
an applicator housing with a head having a pad support portion;
a deformable, liquid-permeable applicator pad with a rear surface connected to the pad support portion and a front surface for contact with a patient's skin in use;
a reservoir of surgical prep liquid being comprised or received in the applicator housing, wherein flow access to the rear surface of the pad is through a generally annular slit; and
wherein an outer wall of an applicator flow conduit has an outwardly-extending flange formation constituting a support for the rear of the pad, a peripheral part of this flange formation being bonded to the rear of the pad to hold the pad in place, whereas inside the bonded part the front surface of the support flange contains a flow distributor plate in a recess corresponding substantially in size and shape to the distribution plate with a flow clearance around its periphery.

17. A surgical prep applicator comprising:
an applicator housing with a head having a pad support portion;
a deformable, liquid-permeable applicator pad with a rear surface connected to the pad support portion and a front surface for contact with a patient's skin in use; and
a reservoir of surgical prep liquid being comprised or received in the applicator housing, wherein flow access to the rear surface of the pad is through a generally annular slit, wherein a slit clearance through which liquid flows to the rear surface of the pad is defined by radial clearance between a portion of the outer periphery of a distributor element and a portion of an inwardly-directed border of an opening of an applicator housing flange in which opening the distributor element sits for liquid flow over an edge portion of said outer periphery.

18. A surgical prep applicator comprising:
an applicator housing including a flange which defines a recess;
an applicator pad which is connected to said applicator housing;
a flow distributor disc positioned between a portion of said applicator pad and a portion of said applicator housing and being received within said recess; and
wherein said flow distributor disc includes an outer edge and wherein said flange and said flow distributor disc cooperate to define a flow path over said outer edge.

19. The surgical prep applicator of claim 18 wherein said flow distributor disc includes an applicator pad-facing surface which defines a flow channel which is open at said outer edge for creating an inward flow path.

20. The surgical prep applicator of claim 19 wherein said flow distributor disc is trapped between said flange and said applicator pad by the connection of said applicator pad to said applicator housing.

21. The surgical prep applicator of claim 18 wherein said recess is annular.

22. The surgical prep applicator of claim 18 wherein said applicator housing includes a flange with a shoulder and said recess is defined in part by a peripheral wall of said shoulder.

23. The surgical prep applicator of claim 18 wherein said applicator housing includes a flange with a shoulder wherein said shoulder is segmented by a lug which contacts said flow distributor disc.

24. The surgical prep applicator of claim 18 wherein said flow path encompasses a majority of said outer edge.

25. A surgical prep applicator comprising:
an applicator housing including a flange which defines a valve seat;
an applicator pad which is connected to said applicator housing; and
a flow distributor disc initially positioned between a portion of said applicator pad and a portion of said applicator housing so as to place said flow distribution disc against a surface of said applicator pad, said flow distributor disc being movable into a sealing position against said valve seat in response to sufficient force on said applicator pad.

26. The surgical prep applicator of claim 25 wherein said flow distributor disc includes an outer edge and wherein said flange and said flow distributor disc cooperate to define a flow path over a portion of said outer edge.

27. The surgical prep applicator of claim 26 wherein said flow distributor disc includes an applicator pad-facing surface which defines a flow channel which is open at said outer edge for creating an inward flow path.

28. A surgical prep applicator comprising:
an applicator housing;
an applicator pad which is connected to said applicator housing; and
a flow distributor disc having an outer peripheral edge and being positioned between a portion of said applicator pad and a portion of said applicator housing, said flow distributor disc further including an applicator pad-facing surface, said applicator pad-facing surface defining a flow channel which is open at a portion of said outer peripheral edge for creating an inward flow path.

29. The surgical prep applicator of claim 28 wherein said applicator housing includes a flange and said flange defines an annular recess wherein said flow distributor disc is received within said annular recess.

30. The surgical prep applicator of claim 28 wherein said applicator housing defines a valve seat and said flow distributor disc is movable into a sealing position against said valve seat in response to sufficient force on said applicator pad.

31. A surgical prep applicator comprising:
an applicator housing with a head having a pad support portion;
a deformable, liquid-permeable applicator pad with a rear surface connected to the pad support portion and a front surface for contact with a patient's skin in use;
a reservoir of surgical prep liquid being comprised or received in the applicator housing, wherein flow access to the rear surface of the pad is through a generally annular slit; and
wherein a front of a distributor element, opposed to the rear surface of the applicator pad, has one or more flow channels whereby liquid may flow from an outer periphery of said distributor element towards the center of the distributor element against the rear surface of the applicator pad.

32. A surgical prep applicator comprising:
an applicator housing including a first portion of a valve;
an applicator pad joined to said applicator housing; and
a second portion of said valve positioned between a portion of said applicator pad and a portion of said applicator housing, said second portion including an outer peripheral edge which in cooperation with said first portion defines a flow path over said outer peripheral edge, said second portion being movable into sealing contact against said first portion, wherein said second portion includes an applicator pad-facing surface which defines a flow channel which is open at said outer edge for creating an inward flow path.

33. The surgical prep applicator of claim 32 wherein said first portion is a flange shoulder.

34. The surgical prep applicator of claim 33 wherein said second portion is a flow distributor disc.

35. The surgical prep applicator of claim 32 wherein said second portion is a flow distributor disc.

36. A surgical prep applicator comprising:
an applicator housing including a flange shoulder;
an applicator pad joined to said applicator housing; and
a flow distributor disc positioned between a portion of said applicator pad and a portion of said applicator housing, said flow distributor disc being movable into sealing contact against said flange shoulder, wherein said flow distributor disc includes an outer peripheral edge which in cooperation with said flange shoulder defines a flow path over a portion of said outer peripheral edge, wherein said flow distributor disc includes an applicator pad-facing surface which defines a flow channel which is open at said outer edge for creating an inward flow path.

* * * * *